US005663377A

United States Patent [19]

Curley, Jr. et al.

[11] Patent Number: 5,663,377
[45] Date of Patent: Sep. 2, 1997

[54] C-GLYCOSIDE ANALOGUES OF N-(4-HYDROXYPHENYL) RETINAMIDE-O-GLUCURONIDE

[75] Inventors: Robert W. Curley, Jr.; Michael J. Panigot, both of Columbus, Ohio

[73] Assignee: The Ohio State Research Foundation, Columbus, Ohio

[21] Appl. No.: 470,232

[22] Filed: Jun. 6, 1995

Related U.S. Application Data

[62] Division of Ser. No. 321,207, Oct. 7, 1994, Pat. No. 5,574,177, and a continuation of Ser. No. 974,730, Nov. 13, 1992, abandoned.

[51] Int. Cl.$^6$ ............................................. C07D 309/14
[52] U.S. Cl. ............................................. 549/417
[58] Field of Search ............................................. 549/417

[56] References Cited

U.S. PATENT DOCUMENTS 4,855,463  8/1989  Barma et al. ............................ 549/417
5,061,723  10/1991  Barua et al.

OTHER PUBLICATIONS

Abstract: "Cancer Chemopreventive Retinoid Metabolites: C–Glucuronide Analogues of 4–Hydroxyphenylretinamide–O–glucuronide" by Panigot et al., presented at the Fourth Chemical Congress of North America, in New York, New York on Aug. 25–30, 1991.

Abstract: "Preparation of C–Glucuronide Analogues of Retinoid O–Glucuronides and Their Preliminary in Vitro Breast Cancer" by Panigot et al., presented at the AAPS Annual Meeting and Exposition in San Antonio, Texas on Nov. 15–19, 1992.

"N–(4–Hydroxyphenyl)retinamide, A New Retinoid for Prevention of Breast Cancer in the Rat" by Moon et al., Cancer Research 39, pp. 1339–1346, Apr. 1979.

"Structure–Activity Relationships of Retinoids in Hamster Tracheal Organ Culture" by Newton et al., Cancer Research 40, pp. 3413–3425, Oct. 1980 by Laboratory of Chemoprevention, National Cancer Institute, Bethesda, Maryland 20205.

"Chemoprevention of Breast Cancer With Retinoids" by Veronesi et al., Journal of the National Cancer Institute Monographs, No. 12, pp. 93–97, 1992.

"Chemical Synthesis of all–trans retinoyl β–glucuronide" by Barua et al., Journal of Lipid Research 26, pp. 1277–1282, 1985 by Department of Biochemistry and Biophysics, Iowa State University, Ames, IA 50011.

"Retinoids in Cancer Treatment" by Tallman et al., The Journal of Clinical Pharmacology 32, No. 10, pp. 868–888, Oct. 1992 by J.B. Lippincott Co., USA.

"Retinoids as Chemopreventive and Anticancer Agents in Intact Animals (Review)" by Hill et al., Anticancer Research 2, pp. 111–124, 1982 by Sourthern Research Institute, Box 3307–A, Birmingham, Alabama 35255.

"Growth Suppression of Human Breast Carcinoma Cells in Culture by N–(4–Hydroxyphenyl)retinamide and its Glucuronide and Through Synergism with Glucarate" by Bhatnager et al., Biochemical Pharmacology, 41, No. 10, pp. 1471–1477, 1991 by Pergamon Press, Great Britain.

"Therapeutic effect of N–(4–Hydroxyphenyl)retinamide on N–methyl–N–nitrosourea–induced Rat Mammary Cancer" by Dowlatshahi et al., Cancer Letters 47, pp. 187–192, 1989 by Elsevier Scientific Publishers Ireland Ltd.

"Effects of Retinoid Glucuronides on Mammary Gland Development in Organ Culture" by Mehta et al., Oncology 48, pp. 505–509, 1991 by S. Karger AG, Basel, Switzerland.

"Putative Metabolites Derived from Dietary Combinations of Calcium Glucarate and N–(4–Hydroxyphenyl)retinamide Act Synergistically to Inhibit the Induction of Rat Mammary Tumors by 7,12–dimethylbenz[α]anthracene" by Abou–Issa et al., Proc. Natl. Acad. Sci. USA 85, pp. 4181–4184, Jun. 1988.

"Effects of Pretreatment with the Retinoid N–(4–Hydroxyphenyl)–all–trans–retinamide and phenobarbital on the Disposition and metabolism of N–(4–Hydroxyphenyl)–all–trans–retinamide in Mice" by Hultin et al., Drug Metabolism and Disposition 16, No. 6, pp. 783–788, 1988.

"Biotransformation and Biological Activity of N–(4–Hydroxyphenyl)retinamide Derivatives in Rodents" by Swanson et al., The Journal of Pharmacology and Experimental Therapeutics 219, No. 3, pp. 632–637, 1981.

"Teratogenicity of N–(4–Hydroxyphenyl)–all–trans–retinamide in Rats and Rabbits" by Kenel et al., Teratogensis, Carcinogenesis, and Mutagenesis 8, pp. 1–11, 1988.

"In vitro interaction of fenretinide with plasma retinol–binding protein and its functional consequences" by Berni et al., Federation of European Biochemical Societies 308, No. 1, pp. 43–45, 1992.

"Tolerability of the Synthetic Retinoid Fenretinide (HPR)" by Costa et al., European Journal of Clinical Oncology 25, No. 5, pp. 805–808, 1989 by Pergamon Press, Great Britain.

"Pharmacokinetics of N–4–Hydroxyphenyl–retinamide and the effect of its oral administration on plasma retinol concentration in cancer patients" by Peng et al., Int. J. Cancer 43, p. 22–26, 1989.

(List continued on next page.)

Primary Examiner—Nicky Chan
Attorney, Agent, or Firm—Calfee Halter & Griswold LLP

[57] ABSTRACT

The present invention provides breast cancer chemopreventive arylamide analogues of retinoic acid, more particularly C-glycoside analogues of N-(4-hydroxyphenyl)retinamide-O-glucuronide that resist both β-glucuronidase mediated enzymatic hydrolysis as well as acid catalyzed hydrolysis. Specifically, the drugs include 4-(retinamido)phenyl-C-glucuronide; 4-(retinamido)phenyl-C-glucoside; 4-(retinamido)benzyl-C-xyloside; 4-(retinamido)benzyl-C-glucoside; 4-(retinamido)benzyl-C-glucuronide; and 4-(retinamido)phenyl-C-xyloside.

14 Claims, No Drawings

OTHER PUBLICATIONS

"Induction of Differentiation of Human Promyelocytic Leukemia Cell Line HL-60 by Retinoyl Glucuronide, a Biologically Active Metabolite of Vitamin A" by Zile et al., *Proc. Nat. Acad. Sci. USA* 84, pp. 2208–2212, Apr. 1987 by Academic Press, Inc.

"Analysis of Water–Soluble Compounds: Glucuronides" by Barua, Arun B., *Method Enzymol.* 189, pp. 136–145, 1990.

"Synthesis of the D–glucuronic acid conjugates of N–(4–hydroxyphenyl)–and N–(2–hydroxyethyl)–retinamides" by Dawson et al., *Carbohydrate Research* 85, pp. 121–129, 1980 by Elsevier Scientific Publishing Co.

"Amino–Substituted β–Benzyl–C–glycosides; Novel β–Glycosidase Inhibitors" by Schmidt et al., *Angew. Chem. Int. Ed. Engl.* 30, No. 10, pp. 1328–1329, 1991.

"The Effective Charges at the Active Sites of Two Glycosidases" by Loeffler et al., *J.C.S. Chem. Comm.*, pp. 984–985, 1974.

"A Review of the Methods of Chemical Synthesis of Sulphate and Glucuronide Conjugates" by Kaspersen et al., *Xenobiotica*, vol. 17, No. 12, pp. 1451–1471, 1987.

Hanessian, Stephen, et al., "Synthesis of Naturally Occuring C–Nucleosides, Their Analogues, and Funcionalized C–Glycosyl Presursors," *Advances in Carbohydrate Chemistry and Biochemistry*, vol. 33, 1976.

"The Chemistry and Biochemistry of C–Nucleosides and C–Aryglycosides" edited by Ellis et al., in *Progress in Medicinal Chemistry 22*, published by Elsevier Science Publishers, B.V. (Biomed. Div.) Oxford, 1985.

"Recent Developments in Synthesis of C–Glycosides" by Postema, Maarten H.D., in *Tetrahedron Report Number 322*, Mar. 12, 1992.

"N–Linked Analogs of Retinoid O–Glucuorindes" by Robarge, et al. *Bioorganic & Medical Chemistry Letters* vol. 4, No. 17, Aug. 1994, pp. 2117–2122.

"N–Linked Analogs of Retinoid O–Glucuorindes" by Robarge, et al. (Abstract) Am. Chemical Society 25th Cent. Reg. Meeting, Oct. 4–6, 1993.

"Synthesis and Evaluation of N–Linked Glycoside Analogs of Retinoic Acid", by Robarge, et al. 27th Annual Mid–Atlantic Symposium, Jul. 1994 (Abstract).

"Synthesis of N–Linked Glycoside Analogs of Retinoic Acid", by Robarge, et al., Am. Chem. Society, Aug. 21–25, 1994.

"N–and C–Glycoside Analogs of Retinoid O–Glucuronides and Their Breast Cancer Inhibitory Potential" by Panigot, et al., XIII Int. Symposium (Paris), Sep. 1994.

"Growth Suppression of Human Breast Carcinoma Cells in Culture by N–(4–Hydroxyphenyl) Retinamide and its Glucuronide and Through Synergism with Glucarate" by Bhatnager, et al., *Biochemical Pharm.*, vol. 41, No. 10, 1991, pp. 1471–1477.

"Chemoprevention of Breast Cancer with Retinoids", Veronesi, et al., J. Nat. Can. Inst. Monographs, No. 12, 1992, pp. 93–97.

"Chemical Synthesis of All–Trans Retinoyl Betaglucuronide" by Barua, et al., J. Lipid Res., vol. 26, 1985, pp. 1277–1282.

"New Synthesis of C–substituted carbohydrates and their derivatives" by Yu, et al., Abstract of Dorklady Akad. Nank. SSSR, 129, 1049–52 (1959) CA:54–8611e (1960).

"Preparation of a glucopyranosylbenzene derivative" by Gerecs, et al., CA:52–11778g (1958) Abstract of Acta Chem. Acad. Sci. Hung. 13, 231–2 (1957).

C-GLYCOSIDE ANALOGUES OF N-(4-HYDROXYPHENYL) RETINAMIDE-O-GLUCURONIDE

This is a divisional of application Ser. No. 08/321,207, filed on Oct. 7, 1994, now U.S. Pat. No. 5,574,177, which is a continuation of No. 07/974,730, filed Nov. 13, 1992 now abandoned.

GRANT REFERENCES

This invention was made with government support under grant number CA49837 awarded by the National Cancer Institute. The government has certain rights in the invention.

BACKGROUND OF THE INVENTION

Breast cancer kills thousands of women annually. While surgical intervention has saved the lives of many women, radical and partial mastectomies often prove physically and emotionally debilitating. Indeed, surgery, even when combined with chemotherapy, may still expose the patient to the threat of possible recurrence.

A drug that promotes the prevention of breast cancer is desirable, and research efforts have been directed to the development of such drugs. For example, retinoic acid, a vitamin A metabolite, and certain retinoic acid analogues, appear to be necessary for the maintenance of normal epithelial tissue differentiation and can reverse the metaplastic condition of hamster tracheal in vitamin A deficient epithelial tissue. (Newton et al. *Cancer Res.* (1980) 40, 3413–3425). As a result, retinoic acid and certain amide analogues have been proposed as cancer chemopreventive agents, and display cancer preventive activity (Moon et al. *Cancer Res.* (1979) 39, 1339–1346). Similarly, retinoic acid analogues such as retinyl acetate, 13-cis-retinoic acid, glucuronide analogues of retinoic acid also display cancer preventive activity, including breast cancer preventative activity (Hill, D. L. et al. *Ann. Rev. Nutrition* (1992) 12, 161–181 and Mehta, R. G. et al. *Oncology* (1991) 48, 1505–1509).

However, a major impediment to developing retinoic acid and its closely related analogues, has been their relatively high toxicity (Biesalski, H. K. *Toxicology* (1989) 57, 117–161). Side effects such as teratogenicity, hepatotoxicity, scaly skin, hair loss and headaches have been observed as a result of the use of most of these compounds. Researchers have been pursuing the synthesis of retinoic acid analogues with increased potency and/or reduced toxicity for application as cancer preventative agents. It has been found that N-(4-hydroxyphenyl) retinamide (hereinafter "4-HPR") displays chemopreventive activity in breast cancer (Moon et al. *Cancer Res.* (1979) 39, 1339–1346). Indeed, 4-HPR when combined with calcium glucarate, synergistically exerts an increased breast cancer chemopreventive activity in carcinogen-induced rat mammary tumors (Abou-Issa, H..M. et al. *Proc. Natl. Acad. Sci. U.S.A.* (1988) 85, 4181–4184). However, the 4-HPR still displays significant cytotoxicity as shown in cultured human breast cancer cells (Bhatnagar, R. et al. *Biochem. Pharmacol.* (1991) 41, 1471–1477).

The glucuronide, N-(4-hydroxyphenyl)retinamide-O-glucuronide (hereinafter "4-HPR-O-glucuronide") has a greater antiproliferative activity and less toxicity in both MCF-7 human mammary cell tumor culture than the 4-HPR. (Bhatnagar, R. et al. *Biochem. Pharmacol.* (1991) 41, 1471–1477.)

However, the 4-HPR-O-glucuronide is unstable; it is hydrolyzed in acidic media and also by the enzyme β-glucuronidase. The propensity to acid hydrolysis may limit the clinical usefulness of 4-HPR-O-glucuronide since oral administration of the drug may reduce the total available concentration of the active drug. Similarly, since β-glucuronidase is present in virtually all mammalian cells, including the blood, liver and intestine, the in vivo half life is quite limited.

It is desirable to have stable chemopreventive drugs, for the prevention and treatment of breast cancer, which resist acid and β-glucuronidase hydrolysis.

SUMMARY OF THE INVENTION

The present invention provides breast cancer chemopreventive and treatment arylamide analogues of retinoic acid, more particularly C-glycoside analogues of N-(4-hydroxyphenyl)retinamide-O-glucuronide that resist both β-glucuronidase mediated enzymatic hydrolysis as well as acid catalyzed hydrolysis. Specifically, the drugs include 4-(retinamido)phenyl-C-glucuronide; 4-(retinamido)phenyl-C-glucoside; 4-(retinamido)benzyl-C-xyloside; 4-(retinamido)benzyl-C-glucoside; 4-(retinamido)benzyl-C-glucuronide; and 4-(retinamido)phenyl-C-xyloside.

DETAILED DESCRIPTION OF THE INVENTION

The present invention provides breast cancer chemopreventive drugs that may also be used for the treatment of cancer, that are arylamide analogues of retinoic acid, more particularly C-glycoside analogues of N-(4-hydroxyphenyl) retinamide-O-glucuronide that are not hydrolysed by acid nor the enzyme β-glucuronidase. Specifically, the drugs include 4-(retinamido)phenyl-C-glucuronide; 4-(retinamido)phenyl-C-glucoside; 4-(retinamido)benzyl-C-xyloside; 4-(retinamido)benzyl-C-glucoside; 4-(retinamido)benzyl-C-glucuronide; and 4-(retinamido)phenyl-C-xyloside. The structure of the analogues is represented below:

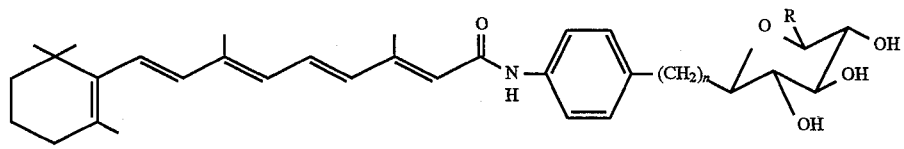

Where R=COOH, $CH_2OH$, or H, and n=0 or 1.

Where R=COOH and n=0, the molecule is 4-(retinamido)phenyl-C-glucuronide. Where R=$CH_2OH$ and n=0, the molecule is 4-(retinamido)phenyl-C-glucoside. Where R=H and n=0, the molecule is 4-(retinamido) phenyl-C-xyloside.

Where R=H and n=1, the molecule is 4-(retinamido) benzyl-C-xyloside. Where R=$CH_2OH$ and n=1, the molecule is 4-(retinamido)benzyl-C-glucoside. Where R=COOH and n=1, the molecule is 4-(retinamido)benzyl-C-glucuronide. A method for preparing a compound comprising the steps of: providing a glycoside wherein all the hydroxy groups are protected; arylating the protected glycoside; then nitrating; reducing the product to its corresponding amine; then retinoylating the product; and then deprotecting the product;

wherein if the glycoside is glucuronic acid, then the product is first oxidized, then protected, before the reduction to the amine. The drugs may be prepared according to the following examples.

PREPARATION OF THE DRUGS

Example 1

4-(Retinamido)phenyl-C-glucuronide

First, 14 g of glucose pentaacetate, from Sigma Chemical Company, was dissolved in 60 ml of 30% HBr in acetic acid and allowed to stand a 4° C. for 69 hours. The acetic acid was removed. The residue was dissolved in 100 ml of chloroform, washed twice with 100 ml of saturated $NaHCO_3$, dried over $MgSO_4$, concentrated, and crystallized from 95% ethanol to give 10.88 g (74%) of acetobromoglucose.

Next, 5.0 g. acetobromoglucose (12.1 mmol) was dissolved in 125 ml of ether and added over 1 hour to phenylmagnesium bromide prepared from 5.6 g (0.23 g atom, 19 equiv.) of magnesium turnings and 25 ml (237 mmol, 19 equiv.) of bromobenzene in 250 ml of ether. The mixture was heated at reflux for 6 hours then poured into 400 ml $H_2O$. The 20 ml glacial acetic acid was added to dissolve the magnesium salts. The mixture was shaken and the layers were separated. The aqueous layer was concentrated to dryness and the residue was reacted with 70 ml of acetic anhydride and 100 ml of pyridine overnight. The mixture was poured into 750 ml $H_2O$ and the precipitate was isolated by filtration and recrystallized from 2-propanol, to yield 2.236 g (45%), of tetra-O-acetylphenyl-C-glucoside.

Next, 1.45 g (3.55 mmol) tetra-O-acetyl phenyl-C-glucoside was stirred with 500 mg $K_2CO_3$ in 50 ml of methanol overnight. The methanol was removed under reduced pressure and the residue was dissolved in 250 ml $H_2O$ containing 1 g. of freshly reduced platinum (IV) oxide. Oxygen was bubbled into the solution which was heated to 80° C. for 24 hours. The catalyst was removed by filtration and the filtrate concentrated to dryness. The residue was heated to reflux in 200 ml of 1% $H_2SO_4$ in methanol for 6 hours. The excess $H_2SO_4$ was neutralized with $NaHCO_3$ and the methanol was removed. The residue was reacted with 70 ml of acetic anhydride and 70 ml of pyridine for 16 hours then poured into 1 L of ice water and the product was isolated by filtration and recrystallized from 2-propanol to yield 724 mg (52%) of methyltri-O-acetyl phenyl-C-glucuronide.

Next, 900 mg (2.28 mmol) of methyl tri-O-acetyl phenyl-C-glucuronide was suspended in 20 ml of acetic anhydride and 4.6 g. (19.8 mmol, 8.7 equiv) of copper (II) nitrate was added. The mixture was heated to 100° C. for 2 hours then poured into 150 ml ice water. The aqueous phase was extracted twice with 75 ml ether. The combined ether extracts were washed four times with 50 ml saturated $NaHCO_3$, dried using $MgSO_4$ and the solvent was removed. The product was purified by flash chromatography using 1:1 ethyl acetate/hexanes as eluant to yield 871 mg (87%) of methyl tri-O-acetyl nitrophenyl-C-glucuronide.

Next, 1.03 g (2.35 mmol) of the mixture of nitrophenyl-C-glucuronides was added to 100 ml of methanol containing 60 mg of 10% palladium on carbon. The mixture was shaken under 40 PSI of hydrogen for 2 hours, then filtered, concentrated, and chromatographed with 1:1 ethyl acetate/hexane as elutant to yield 269 mg (28%) methyl tri-O-acetylamino phenyl-C-glucuronide.

Retinoyl chloride was prepared from 264 mg (0.88 mmol) retinoic acid, and 73 µL of pyridine, 65 µL (0.88 mmol) of thionyl chloride in 10 ml of ether at 0° C. The mixture was allowed to warm to room temperature over 1 hour. Then 360 mg (0.88 mmol) of 4-(methyltri-O-acetyl) aminophenyl-C-glucuronide was added in 15 ml of benzene containing 100 µL of pyridine. The mixture was stirred at room temperature for 72 hours, diluted with 100 ml ether, and washed once with 50 ml water, then washed twice with 50 ml 0.05M $H_2SO_4$, and finally washed twice with 50 ml saturated $NaHCO_3$. The organic layer was dried using $Na_2SO_4$ concentrated, purified by flash chromatography using 1:1 ethyl acetate/hexanes as elutant to yield 379.5 mg (62%) of 4-(methyltri-O-acetyl) retinamidophenyl-C-glucuronide.

Then 600 mg (0.868 mmol) 4-(methyltri-O-acetyl) retinamidophenyl-C-glucuronide was suspended in 10 ml of 0.2M sodium methoxide in methanol and stirred at room temperature overnight. To this mixture was added 600 mg (15 mmol) of sodium hydroxide and 10 ml of $H_2O$, which was then dried using $Na_2SO_4$, then concentrated and chromatographed on RP-18 with 85:15 methanol/$H_2O$ to yield 148 mg (31%) of 4-(retinamido)phenyl-C-glucuronide.

Example 2

4-(Retinamido)phenyl-C-glucoside

First, 14 g of glucose pentaacetate, from Sigma Chemical Company, was converted to 10.88 g of acetobromoglucose as described in Example 1.

Next, 5 g. of the acetobromoglucose (12.1 mmol) was dissolved in 125 ml of ether and added over 1 hour to phenylmagnesium bromide prepared from 5.6 g (0.23 g atom, 19 equiv.) of magnesium turnings and 25 ml (237 mmol, 19 equiv.) of bromobenzene in 250 ml of ether. The mixture was heated at reflux for 6 hours then poured into 400 ml $H_2O$. Then 20 ml glacial acetic acid was added to dissolve the magnesium salts. The mixture was shaken and the layers were separated. The aqueous layer was concentrated to dryness and the residue was reacted with 70 ml of acetic anhydride and 100 ml of pyridine overnight. The mixture was poured into 750 ml $H_2O$ and the precipitate was isolated by filtration and recrystallized from 2-propanol, to yield 2.236 g (45%), of tetra-O-acetylphenyl-C-glucoside.

Next 5.63 g. (13.8 mmol) tetra-O-acetyl phenyl-C-glucoside was dissolved in 150 ml of acetic anhydride and then 25.58 g (110.4 mmol, 8.0 equiv.) copper (II) nitrate was added. The mixture was heated to 100° C. for 1 hour then poured into 400 ml ice water. The organic soluble material was extracted with two ether washes of 200 ml. The ether extracts were washed twice with 10.0 ml water and saturated aqueous sodium bicarbonate, dried using $MgSO_4$ and concentrated to dryness, to yield 6.11 g (97%) of a 1:1 mixture of o- and p-nitrophenyl-C-glucosides.

Next, 1.046 g of the isomeric tetra-O-acetyl nitrophenyl-C-glucoside was dissolved in 150 ml of methanol and about 100 mg of 10% palladium on carbon was added. The mixture was shaken under 40 PSI of hydrogen for 1.5 hours. The catalyst was removed by filtration, the filtrate was concentrated to dryness, and the residue was chromatographed on silica gel using 1:1 ethyl acetate/hexanes as elutant to give 372.2 mg (38%) of 4-(tetra-O-acetyl) aminophenyl-C- glucoside. A sample of this material having a melting point of 110°–111° C. was recrystallized from 2-propanol.

Next, retinoyl chloride was prepared by dissolving 192 mg (0.64 mmol) of retinoic acid in 10 ml of ether containing 100 ml of pyridine and cooled to 0° C. Then 47 μL (0.64 mmol) thionyl chloride was added. The mixture was allowed to come to room temperature over 90 minutes and then 270 mg (0.64 mmol) of the 4-(tetra-O-acetyl) aminophenyl-C-glucoside was added in 9 ml benzene and 1 ml pyridine. The mixture was stirred at room temperature for 40 hours then diluted with 100 ml ethyl acetate and extracted with 100 ml $H_2O$, followed by two washes with 100 ml 1% $H_2SO_4$, and 2 washes with 100 ml saturated aqueous sodium bicarbonate solution. The organic phase was dried using $MgSO_4$, concentrated, and chromatographed with 1:1 ethyl acetate/hexanes as elutant to yield 247 mg (54%) of the 4(tetra-O-acetyl) retinamidophenyl-C-glucoside.

Next, 247 mg (0.35 mmol) 4-(retinamido)phenyl-C-glucoside tetraacetate was dissolved in 20 ml methanol and 0.2 g of potassium carbonate was added. The mixture was stirred at room temperature for 18 hours, concentrated and chromatographed on RP-18 with 1:1 methanol/water then 3:1 methanol/water then 100% methanol, to yield 47.7 mg (25%) of 4-(retinamido)phenyl-C-glucoside.

Example 3

4-(Retinamido)phenyl-C-xyloside

First, 50 g of xylose, from Sigma Chemical Company, 12.5 g of sodium acetate (anhydrous) and 200 ml of acetic anhydride were heated to reflux for 1 hour and poured into 1 L of ice water. Xylose tetraacetate was isolated by filtration and recrystallized from 95% ethanol to yield 56.75 g (54%).

Next, 5 g. (15.7 mmol) of the xylose tetraacetate was dissolved in 200 ml dry chloroform and 8.4 g. (62.8 mmol, 4 equiv), aluminum chloride was added. The mixture was stirred at room temperature for 2 hours, diluted with 200 ml $H_2O$, shaken, and separated. The chloroform layer was washed with 200 ml $H_2O$, then washed twice with 200 ml saturated aqueous $NaHCO_3$, dried using $MgSO_4$, and concentrated, to provide crude acetochloroxylose. The crude acetochloroxylose was dissolved in 100 ml ether and added to a refluxing solution of phenylmagnesium bromide prepared from 18 ml (169 mmol, 10.8 equiv.) of bromobenzene and 4.12 g (0,169 g atom, 10.8 equiv) of magnesium turnings in 250 ml of ether. The mixture was heated at reflux for 5 hours and poured into 150 ml $H_2O$ containing 15 ml of glacial acetic acid. The aqueous layer was concentrated to dryness and the residue was reacted with 75 ml acetic anhydride and 75 ml of pyridine for 20 hours. The mixture was poured into 300 ml $H_2O$. The product was isolated by filtration and recrystallized from 2-propanol, to yield 1.28 g (24%), tri-O-acetylphenyl-C-xyloside having a melting point of 161°–162° C.

Then 1200 mg (3.54 mmol) of the tri-O-acetyl phenyl-C-xyloside was dissolved in 50 ml of acetic anhydride and 6.65 g (28.6 mmol, 8 equiv.) copper (II) nitrate was added. The mixture was heated to 100° C. for 1 hour and then poured into 300 ml of ice water. The water was extracted with 2 washes of 150 ml with ether. The ether extracts were washed twice with 150 ml with water then washed twice with 50 ml saturated $NaHCO_3$, then washed with 50 ml brine, dried using $MgSO_4$ and concentrated to yield 1.347 g (99%) of a 1:1 mixture of o- and p-tri-O-acetyl nitrophenyl-C-xylosides.

Next, 1.35 g. (3.54 mmol) of the mixture of nitrophenyl-C-xylosides was suspended in 50 ml of methanol and 100 mg of 10% palladium on carbon was added. The mixture was shaken under 40 PSI of hydrogen for 1.5 hours. The catalyst was removed by filtration, and the solvent was removed. The residue was purified by flash chromatography using 1:1 ethyl acetate/hexanes as elutant to yield 375 mg (30%) of 4-(tri-O-acetyl) aminophenyl-C-xyloside.

Retinoyl chloride was prepared by dissolving 320 mg (1.07 mmol) retinoic acid suspended in 10 ml ether containing 200 μl of pyridine. The mixture was cooled to 0° C. and 77 μl (1.07 mmol) of thionyl chloride was added. The mixture was allowed to warm to room temperature over 1.5 hours. The acetylated aminophenyl-C-xyloside was suspended in 16 ml benzene and 800 μl pyridine was added. The mixture was stirred at room temperature for 24 hours, diluted with 25 ml of ethyl acetate, and washed three times with 50 ml water, twice with 25 ml with 5% HCl, and twice with 25 ml with saturated $NaHCO_3$, dried using $MgSO_4$, and concentrated. The residue was purified by chromatography using 1:1 ethyl acetate/hexanes as elutant to yield 500 mg (74%) of 4-(tri-O-acetyl) retinamidophenyl-C-xyloside having a melting point 96°–98° C.

Then 480 mg (0.76mmol) acetylated retinamidophenyl-C-xyloside was suspended in 10 ml of methanol and 100 mg (0.72 mmol) of potassium carbonate was added. The mixture was stirred at room temperature overnight, the solvent was removed, and the residue was partitioned between 50 ml ethyl acetate and 50 ml water. The mixture was shaken and the layers separated. The organic layer was dried using $Na_2SO_4$ and the solvent removed. This step yielded 293.5 mg (76%), 4-(retinamido)phenyl-C-xyloside, having melting point 198°–200° C. which was used without further purification.

Example 4

4-(Retinamido)benzyl-C-glucuronide

First, 59 g (109 mmol) of 2,3,4,6-tetra-O-benzyl glucose, from Sigma Chemical Company, was dissolved in 200 ml of pyridine and 22.3 g (120 mmol) of p-nitrobenzoyl chloride was added. The mixture was stirred at room temperature for 72 hours, poured into 750 ml of water, and the solid was isolated by filtration and recrystallized from 95% ethanol to produce 68.8 g (91%) of 2,3,4,6-tetra-O-benzyl-1-p-nitrobenzoyl glucose.

Next, 2.00 g (2.9 mmol) of the 2,3,4,6-tetra-O-benzyl-1-p-nitrobenzoyl glucose was dissolved in 20 ml of dichloromethane and hydrogen bromide was bubbled in for 10 minutes. The p-nitrobenzoic acid was removed by filtration and the filtrate was concentrated to give the crude glycosyl bromide which was dissolved in 50 ml of ether and added to benzylmagnesium chloride prepared from 600 mg (0.0247 g-atom) of magnesium and 2.8 ml (24.3 mmol) benzyl chloride. The mixture was heated at reflux for 4 hours then poured into 100 ml of water containing 5 ml of acetic acid. The mixture was shaken and separated. The ether layer was washed twice with 50 ml saturated $NaHCO_3$, once with 50 ml brine, dried using $MgSO_4$, and concentrated. The residue was dissolved in 80 ml glacial acetic acid containing 0.1 g of 10% palladium on carbon and shaken under 40 PSI of hydrogen for 19 hours. The catalyst was removed by filtration and the filtrate was concentrated to dryness. The residue was acetylated with 30 ml of pyridine and 30 ml of acetic anhydride over 16 hours. The reaction was poured into 100 ml of water and extracted twice with 50 ml of ether. The ether extracts were washed twice with 50 ml water, once with 50 ml 5% HCl, once with 50 ml saturated $NaHCO_3$, once with 50 ml brine. The extracts were dried using MgSO$_4$, concentrated, and crystallized from 2-propanol to yield 194 mg (16%), tetra-O-acetyl benzyl-C-glucoside having a melting point of 118°–119° C.

Next, 1.56 g (3.70 mmol) tetra-O-acetyl benzyl-C-glucoside was dissolved in 30 ml of acetic anhydride and 7.3 g (31.4 mmol, 8.5 equiv) copper (II) nitrate was added. The mixture was heated to 100° C. for 1 hour and poured into 150 ml of ice water. The water was extracted twice with 60 ml of ether. The ether extracts were washed twice with 50 ml water, twice with 50 ml saturated NaHCO$_3$, dried using MgSO$_4$, and concentrated. The crude nitrobenzyl-C-glucoside was dissolved in 30 ml of methanol and 340 mg of potassium carbonate was added. The mixture was stirred at room temperature overnight, concentrated, and dissolved in 100 ml of water containing 1 g of freshly reduced platinum (IV) oxide. The mixture was heated to 80° C. and oxygen was bubbled in for 10 hours. The catalyst was removed by filtration and the filtrate concentrated to dryness. The residue was heated to reflux in 100 ml of 2% H$_2$SO$_4$ in methanol for 1 hour. Excess H$_2$SO$_4$ was neutralized with 10 ml of pyridine. The mixture was concentrated to dryness and the residue was reacted with 30 ml of pyridine and 60 ml of acetic anhydride for 16 hours. The mixture was poured into 300 ml of ice water and extracted twice with 100 ml ether. The ether layers were washed twice with 200 ml with water, once with 100 ml saturated NaCHO$_3$, dried using MgSO$_4$, and concentrated to yield 1.107 g (66%) of a 1 to 1 mixture ortho and para methyl tri-O-acetyl nitrobenzyl-C-glucuronides.

The 1.107 g (2.44 mmol) of the 4-nitrobenzyl-C-glucuronide mixture was dissolved in 100 ml of methanol and 100 mg of 10% palladium on carbon was added. The mixture was shaken under 40 PSI of hydrogen for 1 hour, the catalyst was removed by filtration, and the filtrate was concentrated and chromatographed on silica gel using 1:1 ethyl acetate/hexanes as elutant to yield 310 mg (30%) of methyl tri-O-acetyl-4-aminobenzyl-C-glucuronide.

The retinoylated benzyl-C-glucuronide was prepared as in Example 1. From 219 mg (0.73 mmol) of retinoic acid and 310 mg (0.73 mmol.) of the protected 4-aminobenzyl-C-glucuronide, 303 mg (59%) of the protected retinamidobenzyl-C-glucuronide having a melting point 80°–82° C. was obtained after chromatography.

Next, 200 mg (0.28 mmol) of the protect retinamidobenzyl-C-glucuronide was dissolved in 5 ml MeOH and 33 mg sodium methoxide was added. After stirring at room temperature for 16 hours, 5 ml of water and 25 mg of sodium hydroxide were added. The mixture was stirred for another 5 hours, acidified to pH=1 with 5% HCl, and extracted five times with 25 ml ethyl acetate. The ethyl acetate extracts were combined and washed twice with 100 ml water, twice with 50 ml brine, dried using Na$_2$SO$_4$ and concentrated to yield 74.5 mg (47%) 4-(retinamido)benzyl-C-glucuronide having a melting point of 98°–100° C.

Example 5

4-(Retinamido)benzyl-C-glucoside

First, 500 mg. (1.18 mmol) of tetra-O-acetyl benzyl-C-glucoside from Example 4, was dissolved in 10 ml of acetic anhydride and 2.2 g (9.46 mmol, 8 equiv) copper (II) nitrate was added. The mixture was heated to 100° C. for 1 hour and poured into 75 ml of water. The water was extracted twice with 40 ml of ether. The ether extracts were washed twice with 40 ml water, twice with 40 ml saturated NaHCO$_3$, once with 40 ml brine, then dried using MgSO$_4$, and concentrated. The crude nitro benzyl-C-glucoside was dissolved in 25 ml of methanol containing 50 mg of 10% palladium on carbon and was shaken under 40 PSI of hydrogen for 1 hour. The catalyst was removed by filtration. The filtrate was concentrated and chromatographed on silica gel using 1:1 ethyl acetate/hexanes as elutant, to yield 173.2 mg (33%), 4-(tetra-O-acetyl) aminobenzyl-C-glucoside having a melting point of 145°–146° C.

The retinamide was prepared as in Example 2. From 108 mg (0.36 mmol) retinoic acid and 158 mg (0.36 mmol) acetylated aminobenzyl-C-glucoside, 133 mg (51%) of 4-(tetra-O-acetyl) retinamidobenzyl-C-glucoside was obtained.

Next, 130 mg (0.18 mmol) of acetylated retinamidobenzyl-C-glucoside was dissolved in 8 ml of methanol containing 100 mg of potassium carbonate. The mixture was stirred at room temperature for 16 hours, concentrated, and partitioned between 40 ml of ethyl acetate and 40 ml of water. The mixture was shaken and separated and the ethyl acetate layer was washed twice with 40 ml water, twice with 40 ml brine, dried using Na$_2$SO$_4$ and concentrated, to yield 68 mg (68%) 4-(retinamido)benzyl-C-glucoside.

Example 6

4-(Retinamido)benzyl-C-xyloside

First, 50 g of xylose, from Sigma Chemical Company, was converted to xylose tetracetate as described in Example 3.

Next, 2.07 g (6.5mmol) of the xylose tetracetate was dissolved in 125 ml dry chloroform and 3.3 g (24.8 mmol, 3.8 equiv.) aluminum chloride was added. The mixture was stirred at room temperature for 1.5 hours then washed once with 50 ml saturated NaHCO$_3$, once with 50 ml water, and once with 50 ml brine, then dried using MgSO$_4$, and the solvent removed. The residue was dissolved in 100 ml ether and added to a refluxing solution of benzylmagnesium chloride prepared from 11.5 ml (0.10 mol) of benzyl chloride and 2.43 g (0.1 g-atom) of magnesium in 250 ml of ether. The mixture was kept at reflux for 4 hours then poured into 400 ml H$_2$O containing 20 ml acetic acid. The aqueous layer was concentrated to dryness and the residue reacted with 75 ml acetic anhydride and 75 ml pyridine for 8 hours. The mixture was poured into 400 ml H$_2$O and extracted three times with 160 ml ether. The ether extracts were washed three times with 100 ml saturated NaHCO$_3$, dried using MgSO$_4$, concentrated, and recrystallized from 2-propanol, to yield 989 mg (43%) tri-O-acetyl benzyl-C-xylopyranoside having a melting point of 118°–119° C.

Next, 989 mg (2.82mmol) of tri-O-acetyl benzyl-C-xyloside was dissolved in 25 ml of acetic anhydride and 4.08 g (17.52 mmol, 62 eq) of copper (II) nitrate was added. The mixture was heated to 100° C. for 2 hours and poured into 125.ml of water. The aqueous layer was extracted three times 25 ml with ether and the combined ether extracts were washed six times with 25 ml saturated NaHCO$_3$, dried using MgSO$_4$, and concentrated. This crude material was suspended in 100 ml of methanol containing 100 mg of 10% palladium on carbon. The mixture was shaken under 40 PSI of hydrogen for 1.5 hours, filtered, and solvent removed. The residue was chromatographed using 1:1 ethyl acetate/hexanes as elutant, to yield 160 mg (16%) of a 4-(tri-O-acetyl) amino benzyl-C-xyloside.

Retinoyl chloride was prepared in 10 ml of ether from 131 mg (0.44 mmol) retinoic acid, 60 ul pyridine, and 32 ul of thionyl chloride were stirred at 0° C. for 1 hour then allowed to warm to room temperature over 30 minutes. Then, pyridine 40 µl, 160 mg (0.44 mmol) 4-(tri-O-acetyl) aminobenzyl-C-xyloside, and 10 ml benzene were added. The mixture was stirred at room temperature for 72 hours and diluted with 50 ml of ether. The organic extracts were washed once with 50 ml water, twice with 50 ml of 1% $H_2SO_4$, three times with 50 ml saturated $NaHCO_3$, once with 50 ml brine, dried using $MgSO_4$, and concentrated. The residue was purified by chromatography using 1:1 ethyl acetate/hexanes as elutant, to yield 194.5 mg (70%), 4 (tetra-O-acetyl) retinamidobenzyl-C-xyloside having a melting point of 88°–90° C.

Then 180 mg (0.286 mmol) acetylated retinamidobenzyl-C-xyloside was dissolved in 10 ml of methanol containing 150 mg of potassium carbonate. The mixture was stirred at room temperature overnight, concentrated, and purified on RP-18 reversed phase silica gel with 100% methanol as elutant, to yield 826 mg (55%) 4-(retinamido)benzyl-C-xyloside.

In the above examples, the product from multiple runs of a synthesis step may have been pooled to obtain the quantities used in subsequent steps.

EVALUATION OF THE DRUGS

Stability of the Drugs

To determine the stability of the C-glucopyranosiduronate linkage towards acidic conditions, samples of 4-HPR-O-glucuronide, 4-(retinamido)phenyl-C-glucuronide and 4-(retinamindo)benzyl-C-glucuronide were treated with 0.1N methanolic HCl at 37° C. for 2 hours.

After this time, the O-glucuronide had undergone substantial hydrolysis of the ether linkage to liberate the N-4-hydroxyphenylretinamide and glucuronic acid. However, both the 4-(retinamido)phenyl-C-glucuronide and the 4-(retinamindo)benzyl-C-glucuronide remained essentially intact. Thus, both the C-phenyl and C-benzyl glycosides, which lack the ether linkage, resist acid hydrolysis and would withstand the low pH of the mammalian stomach.

While the 4-HPR-O-glucuronide is hydrolysed to glucuronic acid and the aglycone by β-glucuronidase, the 4-(retinamido)phenyl-C-glucuronide and the 4-(retinamido) benzyl-C-glucuronide are not. This indicates that the 4-(retinamido)phenyl-C-glucuronide and the 4-(retinamido) benzyl-C-glucuronide would not be hydrolyzed by the enzyme in vivo.

Indeed, the 4-(retinamido)phenyl-C-glucuronide and 4-(retinamido)benzyl-C-glucuronide act as inhibitors of β-glucuronidase mediated hydrolysis of N-4-hydroxyphenylretinamide-O-glucuronide to N-4-hydroxyphenylretinamide and glucuronic acid with 4-(retinamido)benzyl-C-glucuronide being slightly more effective than the 4-(retinamido)phenyl-C-glucuronide. The Km value of β-glucuronidase for 4-HPR-O-glucuronide under experimental conditions was determined to be 184.5 µM, using the method of Beinfeld, P. et al., *J. Am. Chem. Soc.*, (1954), 76, 4872–4877. Accordingly, the concentration of the 4-HPR-O-glucuronide in the inhibition study was selected to be below 184.5 µM. The $IC_{50}$ values were determined according to the method of Lang, J. H. et. al. *J. Med. Chem.* (1971), 14, 223–236, using 10% methanol as a co-solvent, for 4-(retinamido)phenyl-C-glucuronide and 4-(retinamido)benzyl-C-glucuronide The $IC_{50}$ values, which represent the concentration of the drug that inhibits the cleavage of 50% of the 4-HPR-O-glucuronide, were found to be 267 µM for the 4-(retinamido)phenyl-C-glucuronide and 236 µM for the 4-(retinamido)benzyl-C-glucuronide. An average typical $IC_{50}$ for glucaro-(1,4)-lactone, one of the most potent inhibitors of the enzyme, is 10 µM. Thus, the $IC_{50}$ values for the C-phenyl and C-benzyl glycosides, indicate that they significantly inhibit β-glucuronidase.

Growth Inhibition of MCF-7 Cells

The antiproliferative activity of the drugs in MCF-7 human mammary tumor cell culture models were determined.

The MCF-7 cells were obtained originally from the Michigan Cancer Foundation. The cells were routinely grown as monolayers in T-25 plastic tissue culture flasks from Falcon, in Oxnard, Calif. containing 5.0 mL of B-10 medium consisting of Minimum Essential Medium (MEM, Earle's Base) supplemented with 1.0 mM MEM non-essential amino acid, 2.0 mM 1-glutamine, 10% fetal bovine serum (FBS), and antibiotics. Culture conditions included a humidified atmosphere of 5% $CO_2$ at 37° C. One-half of the medium was replenished twice a week. Cells were harvested by trypsinization upon confluency. All variables were evaluated in triplicate.

For the growth inhibition assay the MCF-7 cells were plated in 24-well plates at a density of $1.5\times10^4$ cells/cm$^2$. After a 24 hour period and again on day 4, the medium was replaced with treatment medium containing the specified drugs at $10^{-5}$ to $10^{-8}$M in absolute ethanol and added to the cell cultures so that the ethanol concentration did not exceed 0.1%. Control cultures were treated with an equivalent volume of absolute ethanol. On day 7 the cells were harvested by trypsinization and viability was assessed by trypan blue exclusion according to Ueda, H. et al. *Cancer* 1980, 46, 2203–2209. Total cell counts were obtained using a hemocytometer as well as a the Coulter Counter. Growth inhibition, that is, cell survival, was calculated for the various drug concentrations using the equation:

$$\% \text{ inhibition} = 100 - R/C \times 100$$

where R and C are the number of cells in the drug-treated and control cultures, respectively.

The $ED_{50}$ for growth inhibition of the MCF-7 cells by the drugs has been evaluated in three separate assays as shown in Table I.

TABLE I

| GROWTH INHIBITION OF MCF-7 CELLS | |
|---|---|
| DRUG | $ED_{50}$ |
| ASSAY 1 | |
| 4-HPR (control) | 2.8 µM |
| 4-(retinamido)benzyl-C-glucuronide | 6.5 µM |
| 4-(retinamido)benzyl-C-glucoside | 3.4 µM |
| ASSAY 2 | |
| 4-HPR (control) | 1.5 µM |
| 4-(retinamido)benzyl-C-xyloside | 15 µM |
| 4-(retinamido)phenyl-C-glucoside | 27 µM |
| ASSAY 3 | |
| 4-HPR (control) | 33 µM |
| 4-(retinamido)phenyl-C-glucuronide | 50 µM |

The 4-(retinamido)phenyl-C-glucuronide appears to show a potency consistent with its glucoside analogue, retinamidophenyl-C-glucoside. The 4-(retinamido)benzyl-C-glucuronide and its glucoside analogue, 4-(retinamido) benzyl-C-glucose exhibit the best growth inhibition of the cells. The glucuronides and glycosides drugs of the present invention are more effective than the xylosides of the present invention and the benzyl drugs are more active than the phenyl drugs.

Although the mechanism of the drugs is not well understood, it has been shown that active drugs in this class compete with retinoic acid for nuclear receptors for retinoic acid.

Retinoic acid receptors, (RAR) α, β, and γ were expressed using a baculovirus expression system in *Spodoter frugiperda* insect cells. DNA, coding for each receptor was introduced into the genome of the baculovirus which was then introduced into the cultured insect cells. Whole cell extracts were prepared by homogenizing cells in 50 mM Tris buffer at pH 7.4 containing 1.5 mM EDTA, 5 mM dithiothreitol, 300 mM KCl and the protease inhibitors, 1 mM phenylmethylsulfonyl fluoride and 5 ug/ml soybean trypsin inhibitor. The homogenate was subjected to centrifugation at 45,000 rpm for 45 minutes at 4° C. in a Ti 70.1 Beckman rotor. The supernatant fraction was stored at −70° C. until use. For drug competition binding studies, 500 µl portions of the retinoic acid receptor-containing protein extracts were incubated on ice for 3 hours in the presence of 5 nM [$^3$H] trans-retinoic acid, from DuPont-NEN, 50.6 Ci/mmole) (RA)±1 µM of each of the drugs listed in Table II or the equivalent volume of ethanol. Ethanol comprised 3.8% of the final volume in each tube. The [$^3$H]-RA-receptor complexes were separated from free ligand using an hydroxylapatite assay, (Williams, D. et al., *Biochemistry* (1974) 13, 5537–5542, and Dame, et al., *Proc. Natl. Acad. Sci. U.S.A.* (1985) 82, 7825–7829). The quantity of [$^3$H]-RA bound by protein was determined by liquid scintillation counting in 4 ml of Optifluor from Packard, Meridan, Conn. The results are shown in Table II.

TABLE II

| DRUG COMPETITION WITH ($3_H$) RETINOIC ACID EXPRESSED AS PERCENT REDUCTION OF BINDING OF THE ($3_H$) RETINOIC ACID | | | |
|---|---|---|---|
| DRUG* 1 µM | mRARα | mRARβ | mRARγ |
| retinoic acid | 100% | 100% | 100% |
| 4-HPR | 18 | 5 | 7 |
| 4-HPR-O-glucuronide | 14 | 4 | 7 |
| 4-(retinamido)phenyl-C-glucuronide | 48 | 47 | 40 |
| 4-(retinamido)benzyl-C-glucuronide | 67 | 82 | 78 |
| 4-(retinamido)benzyl-C-glucoside | 56 | 64 | 77 |
| 4-(retindmido)benzyl-C-xyloside | 12 | 3 | 2 |
| 13-cis-retinoic acid | 28 | 13 | 4 |

If the drugs of this invention exert their chemopreventative effect by binding to receptors for retinoic acid, then the data supports the preference for 4-(retinamido)phenyl-C-glucuronide, 4-(retinamido)benzyl-C-glucoside and particularly 4-(retinamido)benzyl-C-glucuronide, which significantly compete with retinoic acid for the receptors.

The drugs of the present invention while described as cancer preventatives and cancer treatments, may also be used in the study of cancer, particularly breast cancer.

Having described the invention, we claim:

1. A method for preparing a compound comprising the steps of:

a. providing a glycoside wherein all the hydroxy groups are protected;

b. arylating the protected glycoside;

c. nitrating the product of step b;

d. reducing the product of step c to its corresponding amine;

e. retinoylating the product of step d; and f. deprotecting the product of step e, to provide a C-glycoside analogue of N-(4-hydroxyphenyl) retinamide-O-glucuronide;

wherein if the glycoside is glucuronic acid, then the product of step c is first oxidized, then protected, before the reduction to the amine.

2. The method of claim 1, wherein the compound has the following structure:

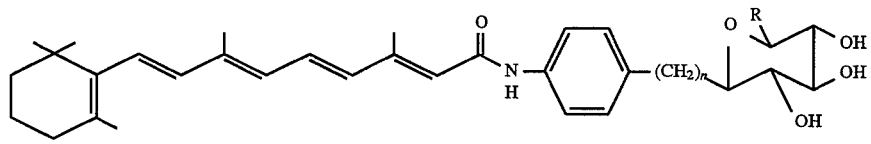

wherein R is an H, COOH, or CH$_2$OH group, and n equals 0 or 1; wherein the glycoside is peracetylated, and the glycoside is selected from the group consisting of: glucose, glucuronic acid, and xylose; and the deprotection of step f is accomplished by deacetylating the product of step e.

3. The method of claim 2, wherein R is an H group, and n equals 0.

4. The method of claim 2, wherein R is a COOH group, and n equals 0.

5. The method of claim 2, wherein R is a CH$_2$OH group, and n equals 0.

6. The method of claim 2, wherein R is an H group, and n equals 1.

7. The method of claim 2, wherein R is a COOH group, and n equals 1.

8. The method of claim 2, wherein R is a CH$_2$OH group, and n equals 1.

9. The method of claim 1, wherein the xylose.

10. The method of claim 1, wherein the glycoside is glucuronic acid.

11. The method of claim 1, wherein the glycoside is glucose.

12. The method of claim 2, wherein the glycoside is xylose.

13. The method of claim 2, wherein the glycoside is glucuronic acid.

14. The method of claim 2, wherein the glycoside is glucose.

* * * * *

UNITED STATES PATENT AND TRADEMARK OFFICE
CERTIFICATE OF CORRECTION

PATENT NO. : 5,663,377
DATED : September 2, 1997
INVENTOR(S) : Curley, Jr., et al.

It is certified that error appears in the above-indentified patent and that said Letters Patent is hereby corrected as shown below:

Col. 12, line 53, after "wherein the" insert --glycoside is--.

Signed and Sealed this

Eleventh Day of November, 1997

Attest:

BRUCE LEHMAN

Attesting Officer

Commissioner of Patents and Trademarks